United States Patent [19]

Batt et al.

[11] Patent Number: 4,971,716

[45] Date of Patent: Nov. 20, 1990

[54] AZEOTROPE-LIKE COMPOSITIONS OF OCTAFLUOROCYCLOBUTANE AND ETHYLENE OXIDE

[75] Inventors: James A. Batt, Depew; Robert G. Richard, Cheektowaga; Ian R. Shankland, Williamsville, all of N.Y.

[73] Assignee: Allied-Signal Inc., Morris Township, Morris County, N.J.

[21] Appl. No.: 425,654

[22] Filed: Oct. 23, 1989

[51] Int. Cl.$^5$ .................. C11D 7/30; C11D 7/50
[52] U.S. Cl. .................. 252/171; 252/153; 252/162; 252/170; 252/172; 252/364; 252/DIG. 9; 422/37
[58] Field of Search ......... 252/162, 170, 171, DIG. 9, 252/364, 153, 172; 422/37

[56] References Cited

U.S. PATENT DOCUMENTS

| | | | |
|---|---|---|---|
| 3,444,085 | 5/1969 | Eiseman | 252/67 |
| 4,057,774 | 11/1977 | Murphy et al. | 252/67 |
| 4,164,471 | 8/1979 | Hutchinson | 252/DIG. 9 |
| 4,437,939 | 3/1984 | Bhise et al. | 203/14 |
| 4,482,465 | 11/1984 | Gray | 252/67 |

FOREIGN PATENT DOCUMENTS 58-079078 5/1983 Japan.
1-139540 6/1989 Japan.

OTHER PUBLICATIONS

Chem. Abstract, 97(12):99211g–Barber et al, *Aiche J.,* 28(1), pp. 138–142 (1982).
Downing, R. C., *Fluorocarbon Refrigerants Handbook,* Prentice Hall (pub), N.J., pp. 139–144.
Patent Application Serial No.: 386,926, filed Jul. 28, 1989.
Patent Application Serial No.: 251,729, filed Oct. 10, 1988.

*Primary Examiner*—Paul Lieberman
*Assistant Examiner*—Linda D. Skaling
*Attorney, Agent, or Firm*—Colleen D. Szuch; J. P. Friedenson

[57] ABSTRACT

Novel azeotrope-like compositions comprising octafluorocyclobutane and ethylene oxide which are particularly useful as sterilizing gases.

10 Claims, No Drawings

AZEOTROPE-LIKE COMPOSITIONS OF OCTAFLUOROCYCLOBUTANE AND ETHYLENE OXIDE

FIELD OF THE INVENTION

This invention relates to novel azeotrope-like mixtures of octafluorocyclobutane and ethylene oxide. These mixtures are useful as gaseous sterilizing agents.

BACKGROUND OF THE INVENTION

Sterilization with a germicidal agent, such as ethylene oxide gas or ethylene oxide gas mixtures, has played an increasingly important role in sterilizing heat or moisture sensitive materials. Rapid growth in the use of sterile, disposable medical devices is just one consequence of gaseous sterilization with agents such as ethylene oxide. The basic gaseous sterilization process consists of evacuating the sterilization chamber, preconditioning the articles to be sterilized at an optimal relative humidity, generally between 20–70% RH, admitting the sterilizing gas at an appropriate pressure and temperature, maintaining contact between the sterilizing atmosphere and the articles to be sterilized for an appropriate time, and finally discharging and evacuating the chamber to remove the sterilant gas.

Although there are many variations on the basic process, the major factors which have to be controlled in order to effect the sterilization are exposure time, temperature, ethylene oxide pressure or partial pressure, and relative humidity The following prior art references provide a good description of the standard sterilization processes and apparatus with which the sterilizing agents of the invention are useful: "Principles and Methods of Sterilization," pp. 501–530, 2d ed. (1969) by J. J. Perkins; "Ethylene Oxide Gaseous Sterilization," pp 181–208, in Industrial Sterilization International Symposium, 1972 U.S. Pat. No. 3,068,064 and U.S. Pat. No. 3,589,861.

By itself, ethylene oxide is an extremely flammable gas. Its flammability range extends from about 3.5% by volume to 100% by volume in air. Thus, when ethylene oxide is used alone as a sterilizing gas, precautions such as explosion proof equipment are mandatory.

A preferable practice is to blend the ethylene oxide with another inert fluid; diluting the ethylene oxide and rendering the mixture as a whole nonflammable. Two such blends which have been used as sterilizing gases are dichlorodifluoromethane (CFC-12)/ethylene oxide and carbon dioxide/ethylene oxide. These blends are non-azeotropic in nature. As such, they suffer the disadvantage of segregation during vaporization which could lead to potentially flammable or explosive situations if process flow rates, outage volumes, etc. are not closely monitored and controlled.

The CFC-12/ethylene oxide blend is generally supplied as a liquid mixture consisting of 88% by weight CFC-12 and 12% by weight ethylene oxide. This composition is below the critical flammability composition of about 14–15% by weight ethylene oxide in CFC-12, and is therefore nonflammable. A typical hospital sterilization process which utilizes the CFC-12/ethylene oxide blend is performed by evacuating the chamber to about 20–24 inches of mercury vacuum, preconditioning the articles at an optimal relative humidity, and filling the chamber to about 10 psig pressure with the gas mixture. Sterilization is generally performed around 130° F. This procedure provides about 630 milligrams of ethylene oxide per liter. The concentration (mg/liter) of ethylene oxide present in the sterilization chamber is critical in determining the required exposure time and ultimate sterilization efficiency. The Association for the Advancement of Medical Instrumentation (AAMI) recommends an absolute minimum ethylene oxide concentration of 450 mg/liter.

A disadvantage of using CFC-12 in such mixtures is that fully halogenated chlorofluorocarbons such as CFC-12 are implicated in causing environmental problems associated with the earth's protective ozone layer.

Although the major purpose of the inert component in these sterilizing gas mixtures is to mask the flammability characteristics of ethylene oxide, simple substitution of an arbitrary nonflammable fluorocarbon does not necessarily ensure a useful sterilizing gas mixture. First, the flammability properties of the blend must be such that sufficient ethylene oxide (mg/liter at a typical pressure and temperature) is delivered by the blend to effect the sterilization in an appropriate time. If the diluent does not mask the flammability to a sufficient extent, a lower concentration of ethylene oxide must be used to ensure non-flammability. In this event, either a longer time period is required to perform the sterilization, which affects productivity, or greater operating pressures are required to increase the ethylene oxide density in the sterilization chamber. Increasing the operating pressure is generally not a viable option because existing sterilization chambers may not be rated for the increased pressure, and as pointed out by Gunther in U.S. Pat. No. 3,589,861, increased pressure can lead to swelling and rupture of the sealed plastic bags commonly used to package disposable medical devices. Indeed, lower operating pressures are advantageous in this respect.

A candidate inert diluent should preferably also be miscible with ethylene oxide in the liquid phase and should not be too highly volatile that it would segregate from the ethylene oxide to anY great extent during vaporization. Segregation or fractionation can lead to potentially flammable or explosive situations. An azeotrope-like mixture would be useful in this context as it does not fractionate by normal evaporation or distillation processes thereby resulting in the release of the flammable ethylene oxide component.

Accordingly, it is an object of this invention to provide a novel sterilizing gas mixture containing ethylene oxide.

It is an object of this invention to provide such a sterilizing gas mixture which contains an inert fluorocarbon diluent which is considered to be stratospherically safe.

Another object of the invention is to provide a sterilizing gas mixture containing ethylene oxide which is azeotrope-like or non-segregating.

Still another object of the invention is to provide a novel sterilizing gas mixture which incorporates all of the above stated objectives.

Other objects and advantages of the invention will become apparent from the following description of the invention.

SUMMARY OF THE INVENTION

The invention relates to novel azeotrope-like compositions comprising octafluorocyclobutane ($C_4F_8$) and ethylene oxide which are useful as sterilizing gases.

DETAILED DESCRIPTION OF THE INVENTION

Octafluorocyclobutane (FC-C-318) is not a chlorinated or brominated halocarbon. As such, it does not contribute to stratospheric ozone depletion. CFC-12, however, a fully halogenated chlorine containing fluorocarbon has been implicated in the depletion of the Earth's protective ozone layer In certain compositional ranges, the vapor or gas mixtures arising from these blends are nonflammable and azeotrope-like. Because of this, the potential for fractionation or separation of components through vaporization, is reduced than is the case with blends of ethylene oxide and CFC-12 or carbon dioxide.

The ethylene oxide component of the invention must be present in effective amounts to accomplish sterilization. However, because ethylene oxide has a flash point less than −20° F., and forms explosive mixtures in air from about 3.0 volume percent to 100 volume percent ethylene oxide, a chemically inert diluent must be added to reduce flammability of the ethylene oxide/air mixture. The primary function of octafluorocyclobutane is to suppress the flammability ethylene oxide. When octafluorocyclobutane is present in effective amounts, this end is achieved.

The azeotrope-like compositions of the invention comprise effective amounts of ethylene oxide octafluorocyclobutane. Preferably, the azeotrope-like compositions of the invention comprise from about 2.0 weight percent to about 18.0 weight percent ethylene oxide and from about 98.0 to about 82.0 weight percent octafluorocyclobutane and exhibits a vapor pressure of about 50 psia±5 psia at 20° C.

A more preferred embodiment of the invention comprises from about 2.5 to about 10.0 weight percent ethylene oxide and from about 90.0 to about 97.5 weight percent octafluorocyclobutane and exhibits a vapor pressure of about 50 psia±about 3 psia at 20.0° C.

The most preferred embodiment of the invention comprises from about 2.5 to about 7.5 weight percent ethylene oxide and from about 92.5 to about 97.5 weight percent octafluorocyclobutane and exhibits a vapor pressure of about 50 psia±about 3 psia at 20.0° C.

The precise or true azeotropic composition has not been determined but has been ascertained to be within the indicated ranges. Regardless of where the true azeotrope lies, all compositions within the indicated ranges, as well as certain compositions outside the indicated ranges, are azeotrope-like, as defined more particularly below.

Vapor compositions within the azeotrope-like regions do not exhibit flame limits in air at ambient conditions as determined by the ASTM E 681-79 method using an electric spark as the ignition source.

From fundamental principles, the thermodynamic state of a fluid is defined by four variables: pressure, temperature, liquid composition, and vapor composition, or P-T-X-Y, respectively. An azeotrope is a unique characteristic of a system of two or more components where X and Y are equal at a stated P and T. In practice this means that the components cannot be separated during evaporation or boiling. Consequently, it is not possible to separate the flammable ethylene oxide component from the blend by evaporation, which could happen if the blend was not azeotrope-like leading to a potentially hazardous situation.

For the purposes of this discussion, by azeotrope-like composition is intended to mean that the composition behaves like a true azeotrope in terms of its constant boiling characteristics or tendency not to fractionate upon boiling or evaporation. Such compositions may or may not be a true azeotrope. Thus, in such systems the composition of the vapor formed during boiling or evaporation is identical or substantially identical to the original liquid composition. Hence, during boiling or evaporation, the liquid composition, if it changes at all, changes only slightly. This is contrasted with non-azeotrope-like compositions in which the liquid composition changes to a substantially during boiling or evaporation.

If the vapor and liquid phases have identical compositions, then it can be shown, on a rigorous thermodynamic basis, that the boiling point versus composition curve passes through an absolute minimum or absolute maximum at this composition. If one of the two conditions, identical liquid and vapor compositions or a minimum or maximum boiling point, are shown to exist, then the system is an azeotrope, and the other condition must follow.

Thus, one way to determine whether a candidate mixture is "azeotrope-like" within the meaning of this invention, is to distill a sample thereof under conditions (i.e. resolution—number of plates) which would be expected to separate the mixture into its separate components. If the mixture is non-azeotropic or non-azeotrope-like, the mixture will fractionate, i.e., separate into its various components with the lowest boiling component distilling off first and so on. If the mixture is azeotrope-like, some finite amount of first distillation cut will be obtained which contains all of the mixture components and which is constant boiling and behaves as a single substance. This phenomenon cannot occur if the mixture is not azeotrope-like i.e. it is not part of an azeotropic system. If the degree of fractionation of the candidate mixture is unduly great, then a composition closer to the true azeotrope must be selected to minimize fractionation.

An equivalent method for determining whether a candidate mixture is azeotrope-like is to determine whether the boiling point versus composition curve passes through a maximum or minimum. Azeotropes which possess a minimum boiling point also possess a maximum in the vapor pressure curve at the same composition; as these blends exhibit positive deviations from Raoult's Law they are termed positive azeotropes. Similarly, those azeotropes which show a maximum boiling point exhibit a minimum in the vapor pressure curve and are termed negative azeotropes owing to the negative deviations from Raoult's Law.

It follows from the above that another characteristic of azeotrope-like compositions is that there is a range of compositions containing the same components in varying proportions which are azeotrope-like. All such compositions are intended to be covered by the term azeotrope-like as used herein. As an example, it is well known that at different pressures, the composition of a given azeotrope will vary at least slightly as does the boiling point of the composition. Thus, an azeotrope of A and B represents a unique type of relationship but with a variable composition depending on temperature and/or pressure.

The FC-C-318/ethylene oxide blends of the present invention exhibit a vapor pressure of about 50 psia±5 psia at 20° F. which is slightly lower than the 64 psia vapor pressure of 88/12 CFC-12/ethylene oxide blend.

The autogenous vapor pressure of the CFC-12/ethylene oxide blend is relied upon to expel the liquid sterilant mixture from a dip-tube in the source cylinder. Although the FC-C-318/ethylene oxide vapor pressure is lower than the CFC-12/ethylene oxide pressure, it is probably sufficient to expel the liquid from the source cylinder. In those instances where the pressure is insufficient, a more volatile component may be added to the system to serve as a propellant and facilitate delivery of the liquid from the cylinder. Examples of such propellants are inert gases such as nitrogen, carbon dioxide, sulfur hexafluoride, perchlorofluorocarbons, hydrochlorofluorocarbons and hydrofluorocarbons.

Compositions incorporating these more volatile, nonflammable, inert components comprise from about 2.0 to about 10.0 weight percent ethylene oxide, from about 5.0 to about 89.0 weight percent octafluorocyclobutane and from about 1.0 to about 33.0 weight percent of a more volatile, nonflammable, inert component. This group of more volatile, nonflammable, inert components would preferably consist of environmentally safe components such as chlorodifluoromethane, 1,2,2,2-tetrafluoroethane, 1,1,2,2-tetrafluoroethane, pentafluoroethane, nitrogen, carbon dioxide and sulfur hexafluoride. The addition of other components to the systems which do not change the essential nature and properties of the systems may be deemed necessary or desirable in specific circumstances.

Below certain temperatures some FC-C-318/ethylene oxide mixtures were found to exhibit two immiscible liquid phases. The highest temperature below which immiscibility occurs is about 12° C. and this only for a mixture containing about 38.0 weight percent ethylene oxide. At compositions away from the 38.0 weight percent ethylene oxide, the immiscibility occurs at even lower temperatures. Above this minimum consolution temperature of 12° C. the system is miscible in all proportions. For the preferred compositions of this invention, 2.5 to 7.5 weight percent ethylene oxide, the immiscible region occurs below about −3° C.

In the process embodiment of the invention, the azeotrope-like compositions of the invention may be used as sterilizing gases in any manner well known in the art by essentially exposing the article to be sterilized to the sterilizing gas under conditions and for a period of time necessary to achieve the desired degree of sterility. Typically, the process is effected by placing the articles to be sterilized in a chamber, humidifying the chamber and exposing the article to the sterilizing gas for an appropriate period of time.

EXAMPLE 1

This example shows that a maximum occurs in the vapor pressure versus composition curve for FC-C-318/ethylene oxide mixtures confirming the existence of an azeotrope. These vapor pressure data are also used to define the constant boiling or azeotrope-like region for the system.

Vapor pressure measurements were performed by preparing FC-C-318/ethylene oxide mixtures in a 240 cc stainless steel vessel equipped with a magnetic stirrer and a calibrated Bourdon-tube pressure gauge accurate to ±0.3%. The stainless steel vessel was submerged in a constant temperature water bath controlled at 20±0.1° C. Mixtures were prepared gravimetrically and the vapor pressure recorded once thermal equilibrium was attained. The vapor pressure versus composition measurements are summarized in Table I.

These data show that addition of ethylene oxide to FC-C-318 increases the vapor pressure above that of the FC-C-318, verifying that an azeotrope is formed between these components. Interpolation between the data indicates that FC-C-318 and ethylene oxide mixtures exhibit a maximum vapor pressure of about 50 psia at 20° C. in the region of 10 to 50 mole percent ethylene oxide. The constant boiling or azeotrope-like composition range corresponds therefore to about 5.0 to about 50.0 mole percent or about 2.0 weight percent to about 18.0 weight percent ethylene oxide.

TABLE I

| Liquid Mixture | | |
|---|---|---|
| Mole Percent Composition FC-C-318 | Mole Percent Composition ethylene oxide | Vapor Pressure (psia) at 20° C. |
| 100.0 | 0.0 | 40.0 |
| 93.0 | 7.0 | 43.8 |
| 86.0 | 14.0 | 46.4 |
| 82.9 | 17.1 | 47.8 |
| 82.2 | 17.8 | 50.0 |
| 71.6 | 28.4 | 49.7 |
| 69.3 | 30.7 | 49.6 |
| 68.8 | 31.2 | 50.1 |
| 68.2 | 31.8 | 49.7 |
| 64.9 | 35.1 | 50.1 |
| 59.5 | 40.5 | 49.6 |
| 53.2 | 46.8 | 49.7 |
| 49.7 | 50.3 | 49.4 |
| 28.9 | 71.1 | 49.1 |
| 0.0 | 100.0 | 21.2 |

EXAMPLE 2

The vapor flammability properties of the various ethylene oxide blends are assessed in this example.

Vapor flammability data were measured at 1 atmosphere pressure and ambient temperature using the ASTM E 681-79 method with an ignition source consisting of a high voltage spark gap. The ternary flammability diagram was developed by preparing mixtures of ethylene oxide, halocarbon and air by the method of partial pressures and then determining whether or not a flame would propagate as defined by ASTM E 681-79. The critical flammability ratio (or composition), i.e., the composition of the fluorocarbon/ethylene oxide blend which contains the maximum amount of ethylene oxide, yet does not exhibit flame limits in air, was determined in a graphical manner similar to that described by Haenni et al., in "Industrial and Engineering Chemistry," Vol. 51, pp. 685–688 (1959).

Critical flammability compositions for mixtures of ethylene oxide/CFC-12 and ethylene oxide/FC-C-318 are listed in Table II.

TABLE II

| Halocarbon | Mole % ethylene oxide | Weight % ethylene oxide |
|---|---|---|
| CFC-12 | 33.3 | 15.4 |
| FC-C-318 | 27.0 | 7.5 |

The critical flammability composition for CFC-12/ethylene oxide was found to be 15.4 weight percent ethylene oxide. This corresponds quite well with the work of Haenni et al., who measured 16.0 weight percent ethylene oxide. Vapor phase FC-C-318 mixtures containing less than 27.0 mole percent or 7.5 weight percent ethylene oxide are nonflammable according to this test method. This composition range is part of the azeotrope-like region identified in the previous example.

EXAMPLE 3

This example shows that nonflammable, azeotrope-like FC-C-318/ethylene oxide blends make available more ethylene oxide than the AAMI recommended minimum ethylene oxide concentrations.

The 88/12 by weight CFC-12/ethylene oxide composition is lower than the measured critical flammability composition by about 20%. If, for example, we reduce the ethylene oxide composition from the FC-C-318 critical flammability composition by the same factor, i.e., consider a 94 percent by weight FC-C318 and 6 percent by weight ethylene oxide blend, then we can compare the ethylene oxide available in the gas phase from these blends by performing ideal gas calculations. For this particular example we will assume that the sterilization chamber was initially evacuated to 22 in Hg vacuum. Results of these calculations are summarized in Table III.

TABLE III

| | Ethylene oxide vapor composition | | |
|---|---|---|---|
| | Weight % | Mole % | mg/liter |
| FC-C-319/ ethylene oxide | 6.0 | 22.5 | 522.0 |
| CFC-12/ ethylene oxide | 12.0 | 27.2 | 631.5 |

This table shows that slightly less gaseous ethylene oxide is available for sterilization from the FC-C-318/ethylene oxide blend than from the CFC-12/ethylene oxide blend. However, it is more than sufficient to meet the AAMI 450 mg/liter minimum recommendation.

What is claimed is:

1. Azeotrope-like compositions consisting essentially of from about 2.0 weight percent to about 18.0 weight percent ethylene oxide and from about 82.0 weight percent to about 98.0 weight percent octafluorocyclobutane which exhibit a vapor pressure of about 50 psia at 20° C.

2. The azeotrope-like compositions of claim 1 wherein said compositions contain from about 10.0 weight percent ethylene oxide and from about 90.0 to about 97.5 weight percent octafluorocyclobutane which exhibit a vapor pressure of about 50 psia at 20° C.

3. The azeotrope-like compositions of claim 1 wherein said compositions contain from about 2.5 weight percent to about 7.5 weight percent ethylene oxide which from about 92.5 to about 97.5 weight percent octafluorocyclobutane and exhibit a vapor pressure of about 50 psia at 20° C.

4. The azeotrope-like compositions of claim 1 wherein said compositions contain from about 2.0 to about 10.0 weight percent ethylene oxide, from about 65.0 to about 89.0 weight percent octafluorocyclobutane and from about 1.0 to about 33.0 weight percent of a more volatile, nonflammable, inert component selected from the group consisting of chlorodifluoromethane, 1,2,2,2-tetrafluoroethane, 1,1,2,2-tetrafluoroethane, pentafluoroethane, nitrogen, carbon dioxide, and sulfur hexafluoride.

5. The azeotrope-like compositions of claim 1 wherein said compositions exhibit a vapor pressure of about 50±5 psia at 20 C.

6. The azeotrope-like compositions of claim 1 wherein said compositions exhibit a vapor pressure of about 50±about 3 psia at 20 C.

7. A method of sterilizing articles comprising preconditioning the articles to be sterilized at an optimal relative humidity and exposing the articles to the sterilizing gas composition of claim 1 under conditions and for a period of time necessary to achieve the desired degree of sterility.

8. A method of sterilizing articles comprising preconditioning the articles to be sterilized at an optimal relative humidity and exposing the articles to the sterilizing gas composition of claim 2 under conditions and for a period of time necessary to achieve the desired degree of sterility.

9. A method of sterilizing articles comprising preconditioning the articles to be sterilized at an optimal relative humidity and exposing the articles to the sterilizing gas composition of claim 3 under conditions and for a period of time necessary to achieve the desired degree of sterility.

10. A method of sterilizing articles comprising preconditioning the articles to be sterilized at an optimal relative humidity and exposing the articles to the sterilizing gas composition of claim 4 under conditions and for a period of time necessary to achieve the desired degree of sterility.

* * * * *

UNITED STATES PATENT AND TRADEMARK OFFICE
CERTIFICATE OF CORRECTION

PATENT NO. : 4,971,716

DATED : November 20, 1990

INVENTOR(S) : James A. Batt, Robert G. Richard and Ian R. Shankland

It is certified that error appears in the above-identified patent and that said Letters Patent is hereby corrected as shown below:

Please amend column 8, lines 9 - 18 as follows:

[The azeotrope-like] <u>Azeotrope-like</u> compositions [of claim 1 wherein said compositions contain] <u>consisting essentially of</u> from about 2.0 to about 10.0 weight percent ethylene oxide, from about 65.0 to about 89.0 weight percent octafluorocyclobutane and from about 1.0 to about 33.0 weight percent of a more volatile, nonflammable, inert component selected from the group consisting of chlorodifluoromethane, 1,2,2,2-tetrafluoroethane, 1,1,2,2-tetrafluoroethane, pentafluoroethane, nitrogen, carbon dioxide, and sulfur hexafluoride.

Signed and Sealed this

Twenty-second Day of June, 1993

Attest:

MICHAEL K. KIRK

*Attesting Officer*  *Acting Commissioner of Patents and Trademarks*